United States Patent

Kidani et al.

[11] 4,255,347
[45] Mar. 10, 1981

[54] PLATINUM COMPLEX

[75] Inventors: Yoshinori Kidani, 2-718, Mataho Kodan-jutaku, 2-1, Mataho-cho, Nishi-ku, Nagoya-shi; Koji Okamoto, Toyota; Reiko Saito, Toyoake, all of Japan

[73] Assignee: Yoshinori Kidani, Nagoya, Japan

[21] Appl. No.: 71,629

[22] Filed: Aug. 31, 1979

[30] Foreign Application Priority Data

Sep. 2, 1978 [JP] Japan .................. 53/107776

[51] Int. Cl.³ .............................................. C07F 15/00
[52] U.S. Cl. ...................... 260/429 R; 260/345.9 R; 424/203; 424/287
[58] Field of Search .................... 260/429 R

[56] References Cited

U.S. PATENT DOCUMENTS

| | | | |
|---|---|---|---|
| 4,115,418 | 9/1978 | Gale et al. | 260/429 R |
| 4,140,707 | 2/1979 | Cleare et al. | 260/429 R |
| 4,169,846 | 10/1979 | Kidani et al. | 260/429 R |

OTHER PUBLICATIONS

Connors et al., Platinum Coordination Complexes in Cancer Chemotherapy, Springer-Verlag, N.Y., p. 20 (1974), Nature 222 385(1969).
Platinum Metal Rev. 15 (2) 42–51 (1971).
Platinum Metal Rev. 17 (1) 2–13 (1973).

Primary Examiner—Helen M. S. Sneed
Attorney, Agent, or Firm—Wolder, Gross & Yavner

[57] ABSTRACT

New platinum complex represented by the general formula [I]:

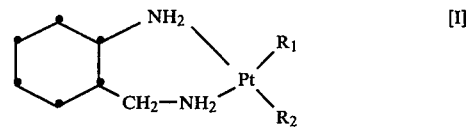

wherein
$R_1$ and $R_2$ are same and represent halogen atom or $NO_3$, or
$R_1$ is $SO_4$ and $R_2$ is $H_2O$, or
$R_1$ and $R_2$ are bonded with each other to form either

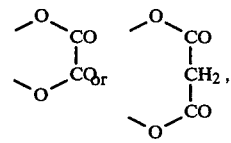

and the configuration of 1-aminomethyl-2-aminocyclohexane is selected from trans-1, trans-d, cis-1 and cis-d.

The compounds of the formula [I] are active against tumor and are expected to be useful as medicaments.

1 Claim, 12 Drawing Figures

PLATINUM COMPLEX

SUMMARY OF THE INVENTION

This invention relates to a new platinum complex represented by the general formula [I]:

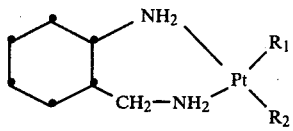

wherein $R_1$ and $R_2$ are same and represent halogen atom or $NO_3$, or $R_1$ is $SO_4$ and $R_2$ is $H_2O$, or $R_1$ and $R_2$ are bonded with each other to form either

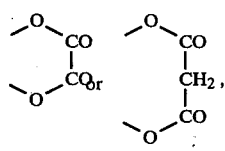

and the configuration of 1-aminomethyl-2-aminocyclohexane [hereinafter referred to as aamch] is selected from trans-l, trans-d, cis-l and cis-d.

The compounds of the formula [I] are active against P-388 tumour and are expected to be useful as medicaments.

It is known that certain platinum complexes are active against tumour cells [for example, Nature, 222, 385 (1969); Platinum Metal Rev., 15, No. 2, 42-51 (1971); ibid. 17, No. 1, 2-13 (1973) and U.S. Pat. No. 4,115,418 (1978)]. It has now been found that new platinum complexes exhibit excellent anti-tumour effect and low toxicity. Thus, the present invention is directed to provide new platinum complexes having improved biological properties.

The platinum complexes provided by the present invention may be produced in the following manner. Racemic modification of trans (or cis)-cyclohexane-1,2-dicarboxylic acid

---

Step I ↓     Introduction of amino group
Rac-trans (or cis)-2-aminocyclohexanecarboxylic acid
    Step II ↓     Conversion into ester
Rac-trans (or cis) 2-aminocyclohexanecarboxylic ethyl ester
    Step III ↓     Conversion into hydrazide
Rac-trans (or cis)-2-aminocyclohexanecarbohydrazide
    Step IV ↓     Conversion into aminomethyl-compound
Rac-trans (or cis)-1-aminomethyl-2-aminocyclohexane
[hereinafter referred to as rac-trans (or cis)-aamch]
    Step V ↓     Optical resolution
Trans-d-aamch . diastereomer and trans- l-aamch . diastereomer
[or cis-d-aamch . diasteromer and cis-l-aamch . diastereomer]
    Step VI ↓     Decomposition of diastereomer
Trans-l-aamch (absolute configuration: 1R, 2S)
Trans-d-aamch (absolute configuration: 2S, 2R)
Cis-l-aamch (absolute configuration: 1R, 2R)
Cis-d-aamch (absolute configuration: 1S, 2S)

---

Full details of the above-mentioned steps are given as follows.

[Step I]

A racemic modification of trans (or cis)-cyclohexane-1,2-dicarboxylic acid is dissolved in a suitable solvent such as, for example, chloroform, added with an acid and the reaction is carried out to introduce an amino group by using a suitable agent such as, for example, sodium azide. After completion of the reaction, the solvent is removed from the reaction mixture which is then added with a neutralizing agent. After the neutralizing, the solution is filtered and the filtrate is concentrated under reduced pressure to dryness, and if desired, recrystallized from ethanol. As the starting material, one of the market grade may be used.

[Step II]

The racemic modification of trans (or cis)-2-aminocyclohexanecarboxylic acid prepared by Step I is dissolved in a suitable solvent such as, for example, ethanol. The solution is saturated with hydrogen chloride and at the same time the refluxing ethanol is removed. After this, water is added to the solution which is neutralized with a neutralizing agent and is extracted with ether. Ether is distilled off from the extract to obtain the desired product.

[Step III]

Hydrazine hydrate is added to the trans (or cis)-2-aminocyclohexanecarboxylic acid prepared by Step II. The solution is refluxed to complete the reaction, and the reaction mixture is concentrated to dryness under reduced pressure to obtain the desired product which may, if desired, be washed with an organic solvent.

[Step IV]

The trans (or cis)-2-aminocyclohexanecarbohydrazide is dissolved in a suitable solvent such as, for example, benzene, ether, tetrahydrofuran and the like. The solution is added with a reducing agent such as, for example, lithium alminium hydride and refluxed for 4 to 7 days. After completion of the reaction, the excessive lithium alminum hydride is decomposed and the solvent is distilled off, followed by concentration to dryness under reduced pressure to obtain the desired product.

[Step V]

Equimolar amounts of rac-trans (or cis)-aamch prepared by Step IV and (+) [or (−)]-dibenzoyltartaric acid are suspended in water and stirred. After completion of the reaction, the resultant diastereomer is dissolved in a solvent of water/methanol (1:1 volume by volume) and allowed to stand for a night to obtain the needles of the desired product.

[Step VI]

Each isomeric diastereomer prepared by Step V is duspended or dissolved in water and is then added with conc. hydrochloric acid. The reaction solution is filtered to give a filtrate which is then neutralized to liberate the desired product. This product is, if desired, extracted with an organic solvent and the solvent is evaporated off to obtain the desired product i.e. trans-d, trans-l, cis-d or cis-l-aamch.

[Step VII]

The production of platinum complexes from the diamines prepared by Step VI may be carried out in a similar manner to that described, for example, in Journal of Pharmaceutical Sciences, vol. 65, 315–328 (1976) by the following procedures.

(1) PtCl$_2$(aamch) is produced by the reaction of K$_2$PtX$_4$ (wherein X is halogen) with aamch.

(2) The PtCl$_2$(aamch) prepared by (1) is reacted with AgNO$_3$ and is then filtered to obtain a filtrate. This filtrate is concentrated to dryness to obtain Pt(NO$_3$)$_2$(aamch).

(3) Pt(NO$_3$)$_2$(aamch) is dissolved in water which is then added with KI, KBr, potassium oxalate, sodium malonate or sodium glucuronate to carry out the reaction, resulting in PtI$_2$(aamch), PtBr$_2$(aamch), Pt(oxalate)(aamch), Pt(malonate)(aamch) or Pt(glucuronate)(aamch) respectively.

(4) PtCl$_2$(aamch) is added with AgSO$_4$ to carry out the reaction. The resultant AgCl is removed by filtration, and the filtrate is evaporated off to obtain Pt(OH$_2$)(SO$_4$)(aamch).

These reactions may be carried out in water, if desired, at an elevated temperature and/or in darkness, and may be completed in 3 to 48 hours to give precipitates coloured usually in white to yellow. The resultant precipitates may be recrystallized from 0.1 N hydrochloric acid to obtain the desired products in the form of crystals.

The compounds of the present invention are prepared by the processes of the examples as hereinafter described and their physical characteristics are indicated in the following table. Malonate, glucuronate and oxalate are hereinafter abbreviated as mal, gluc and OX respectively.

Experiments

CDF$_1$ mouse (each group consisting of 6 mouse) were used as test animals. A physiological sodium chloride solution containing 10$^6$ cells of Leukemia P-388 was administered to each mice intraperitoneally. On the first and fifth days after this, each mice was intraperitoneally administered with a given amount of the test compound contained in physiological sodium chloride solution to obtain the results shown in Table 2 wherein the effect is indicated by T/C % (the ratio of the median survival days of the test animal to the control mice).

For comparison purpose, PDD i.e. cis-dichlorodiammine platinum (II) which is represented by the following formula:

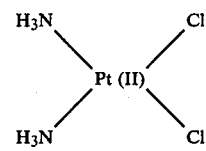

and which is known as being active against tumour cells is treated in a similar manner to that described above to obtain the results shown as Reference in the following tables, from which it is apparent that the platinum complexes provided by the present invention are superior to the known platinum complex with respect to T.I., toxicity and other properties.

TABLE 1

W: white, LY: light yellow, Y: yellow,

| | | | Elemental analysis | | | | | |
| | | Col- | Found | | | Calculated | | |
| No. | Compound | our | H | C | N | H | C | N |
|---|---|---|---|---|---|---|---|---|
| 1 | PtCl$_2$(trans-d-aamch) | W | 4.10 | 21.32 | 7.11 | 4.18 | 20.98 | 6.88 |
| 2 | PtCl$_2$(trans-l-aamch) | " | " | " | " | 3.96 | 21.09 | 6.97 |
| 3 | PtCl$_2$(cis-d-aamch) | " | " | " | " | 4.14 | 21.71 | 7.20 |
| 4 | PtCl$_2$(cis-l-aamch) | " | " | " | " | 3.98 | 21.20 | 6.96 |
| 5 | PtBr$_2$(trans-d-aamch) | LY | 3.34 | 17.40 | 5.80 | 3.45 | 18.13 | 5.97 |
| 6 | PtBr$_2$(trans-l-aamch) | " | " | " | " | 3.27 | 17.62 | 5.69 |
| 7 | PtBr$_2$(cis-d-aamch) | " | " | " | " | 3.36 | 17.75 | 5.95 |
| 8 | PtBr$_2$(cis-l-aamch) | " | " | " | " | 3.28 | 17.60 | 5.74 |
| 9 | PtI$_2$(trans-d-aamch) | Y | 2.80 | 14.57 | 4.85 | 2.95 | 15.93 | 5.45 |
| 10 | PtI$_2$(trans-l-aamch) | " | " | " | " | 2.88 | 15.32 | 4.90 |
| 11 | PtI$_2$(cis-d-aamch) | " | " | " | " | 2.88 | 14.75 | 4.64 |
| 12 | PtI$_2$(cis-l-aamch) | " | " | " | " | 2.80 | 14.75 | 4.88 |
| 13 | Pt(OX)(trans-d-aamch) | W | 3.93 | 26.28 | 6.81 | 3.84 | 26.50 | 6.89 |
| 14 | Pt(OX)(trans-l-aamch) | " | " | " | " | 3.78 | 25.82 | 6.82 |
| 15 | Pt(OX)(cis-d-aamch) | W | 3.93 | 26.28 | 6.81 | 3.82 | 26.12 | 7.00 |
| 16 | Pt(OX)(cis-l-aamch) | " | " | " | " | 3.90 | 26.02 | 6.84 |
| 17 | Pt(OH$_2$)(SO$_4$)(trans-d-aamch) | " | 4.16 | 19.22 | 6.41 | | | |
| 18 | Pt(OH$_2$)(SO$_4$)(trans-l-aamch) | " | " | " | " | 4.14 | 19.15 | 6.10 |
| 19 | Pt(OH$_2$)(SO$_4$)(cis-d-aamch) | " | " | " | " | 4.00 | 19.35 | 6.08 |
| 20 | Pt(OH$_2$)(SO$_4$)(cis-l-aamch) | " | " | " | " | 4.22 | 19.25 | 6.61 |
| 21 | Pt(NO$_3$)$_2$(cis-d-aamch) | " | 3.61 | 18.79 | 12.53 | 3.40 | 18.76 | 12.44 |
| 22 | Pt(NO$_3$)$_2$(cis-l-aamch) | " | " | " | " | 3.57 | 18.91 | 12.38 |
| 23 | Pt(NO$_3$)$_2$(trans-d-aamch) | " | | | | | | |
| 24 | Pt(NO$_3$)$_2$(trans-l-aamch) | " | | | | | | |
| 25 | Pt(mal)(trans-d-aamch) | " | 4.27 | 28.23 | 6.59 | 4.08 | 28.05 | 6.62 |
| 26 | Pt(mal)(trans-l-aamch) | " | | | | | | |
| 27 | Pt(mal)(cis-d-aamch) | " | | | | | | |
| 28 | Pt(mal)(cis-l-aamch) | " | | | | | | |
| 29 | Pt(gluc)(trans-d-aamch) | LY | | | | | | |
| 30 | Pt(gluc)(trans-l-aamch) | " | | | | | | |
| 31 | Pt(gluc)(cis-d-aamch) | " | | | | | | |
| 32 | Pt(gluc)(cis-l-aamch) | " | | | | | | |

The following experiments were conducted to investigate the anit-tumour activities of the compounds provided by the present invention.

TABLE 2

D : Dosis (mg/kg)
No.: Compound number

| D No. | 100 | 50 | 25 | 12.5 | 6.25 | 3.12 | 1.56 | 0.78 | 0.39 |
|---|---|---|---|---|---|---|---|---|---|
| | | | | T/C % | | | | | |
| 1 | | | 61 | 68 | 226 | 174 | 157 | 156 | 138 | 
| | | | | | | | | | 123 |
| 2 | | | 612 | 81 | 197 | 177 | 162 | 159 | 140 |
| | | | | | | | | | 118 |
| 3 | | | | 106 | 242 | 187 | 166 | 147 | 135 |
| 4 | | | | 90 | 240 | 203 | 157 | 138 | 110 |
| 5 | 70 | 194(1) | 188 | 175 | 161 | 146 | 134 | 133 | |
| 6 | 80 | 186 | 178 | 178 | 166 | 164 | 135 | 130 | |
| 7 | 75 | 190 | 196 | 161 | 161 | 147 | 144 | 125 | |
| 8 | 67 | 99 | 181 | 178 | 176 | 147 | 154 | 135 | |
| 9 | 160 | 160 | 143 | 145 | | | | | |
| 10 | 0 | 153 | 158 | 138 | 128 | | | | |
| 11 | 0 | 73 | 160 | 158 | 141 | | | | |
| 12 | 0 | 80 | 141 | 148 | | | | | |
| 13 | | | 171 | 168 | 139 | 131 | 112 | | |
| 14 | | | 83 | 245 | 200 | 151 | 126 | 128 | |
| 15 | | | 90 | 184 | 184 | 131 | 128 | 128 | |
| 16 | | 70 | 193 | 163 | 137 | 146 | 131 | | |
| 17 | | 215 | 196 | 179 | 185 | 166 | 140 | 129 | |
| 18 | | | 80 | 181 | 181 | 151 | 158 | 146 | |
| 19 | | 59 | 85 | 189 | 174 | 152 | 159 | | |
| 20 | | 59 | 88 | 189 | 178 | 159 | 133 | | |
| 21 | | | | 248 | 228 | 197 | | | |
| 22 | | | | 92 | 240 | 220 | | | |
| 29 | | | 170 | 170 | 148 | | | | |
| 30 | | | 200 | 173 | 158 | | | | |
| 31 | | | 180 | 179 | 167 | | | | |
| 32 | | | 208 | 184 | 173 | | | | |
| Ref. | | | 0 | 0 | 67 | 121 | 230 | 165 | 134 |
| | | | | | | | | | 118 |

The toxic dose (T.D), optimal dose (O.D), minimal effective dose (MED), each T/C% corresponding to O.D or MED respectively, and therapeutic index (T.I) of each compound are calculated on the basis of Table 2 and shown in Table 3.

TABLE 3

| No. | T.D. mg/kg | O.D mg/kg | O.D T/C % | MED mg/kg | MED T/C% | T.I |
|---|---|---|---|---|---|---|
| 1 | 25 | 12.5 | 226 | 0.39 | 123 | 32 |
| 2 | 25 | 12.5 | 197 | 0.78 | 126 | 16 |
| 3 | 25 | 6.25 | 242 | 0.39 | 135 | 16 |
| 4 | 25 | 6.25 | 240 | 0.78 | 138 | 8 |
| 5 | 100 | 50 | 194(1) | 0.78 | 133 | 64 |
| 6 | 100 | 50 | 186 | 0.78 | 130 | 64 |
| 7 | 100 | 25 | 196 | 0.78 | 125 | 32 |
| 8 | 100 | 25 | 181 | 0.78 | 135 | 32 |
| 9 | ≧200 | 100 | 160 | 12.5 | 145 | 8 |
| 10 | 100 | 25 | 158 | 6.25 | 128 | 4 |
| 11 | 50 | 25 | 160 | 6.25 | 141 | 4 |
| 12 | 50 | 12.5 | 148 | 12.5 | 148 | 1 |
| 13 | ≧50 | 25 | 171 | 3.12 | 131 | ≧8 |
| 14 | 25 | 12.5 | 245 | 0.78 | 128 | 16 |
| 15 | 50 | 12.5 | 184 | 0.78 | 128 | 16 |
| 16 | 50 | 25 | 193 | 1.56 | 131 | 16 |
| 17 | ≧100 | 50 | 215 | 0.78 | 129 | 64 |
| 18 | 75 | 12.5 | 181 | 0.78 | 146 | 16 |
| 19 | 25 | 6.25 | 189 | ≦0.78 | 159 | ≧8 |
| 20 | 25 | 6.25 | 189 | 0.78 | 138 | 8 |
| Ref | 12.5 | 3.12 | 230 | 0.78 | 134 | 4 |

With reference to the accompanying drawings.

Figure 10:
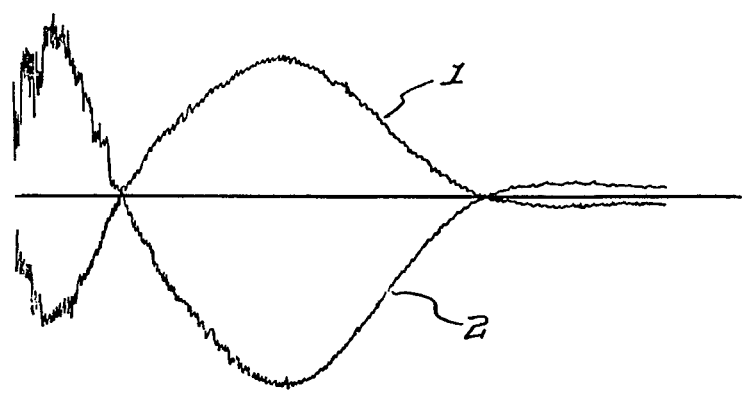

FIG. 10 (1) and FIG. 10 (2) show respectively CD spectra of Pt(OH$_2$)(SO$_4$)(trans-l-aamch) and Pt(OH$_2$)(SO$_4$)(trans-d-aamch).

Figure 12:
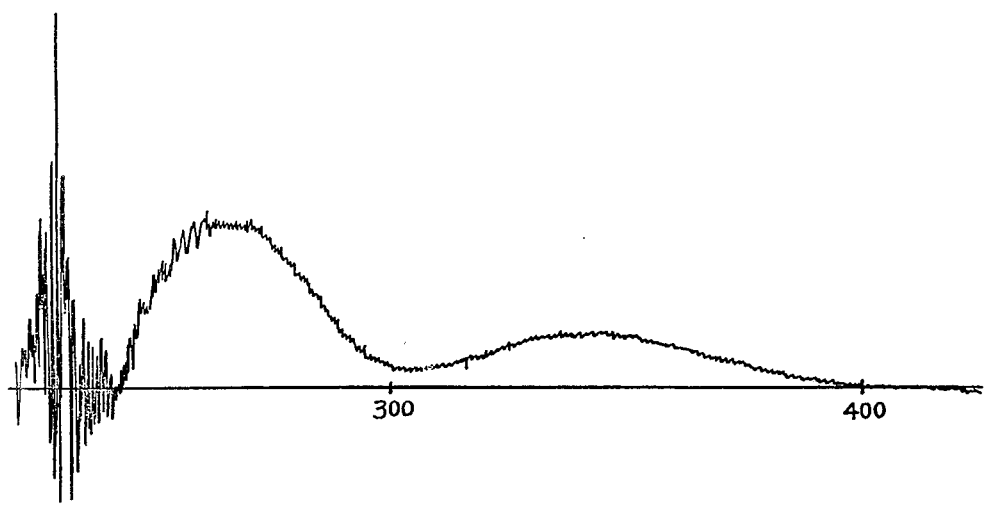
Figure 11:
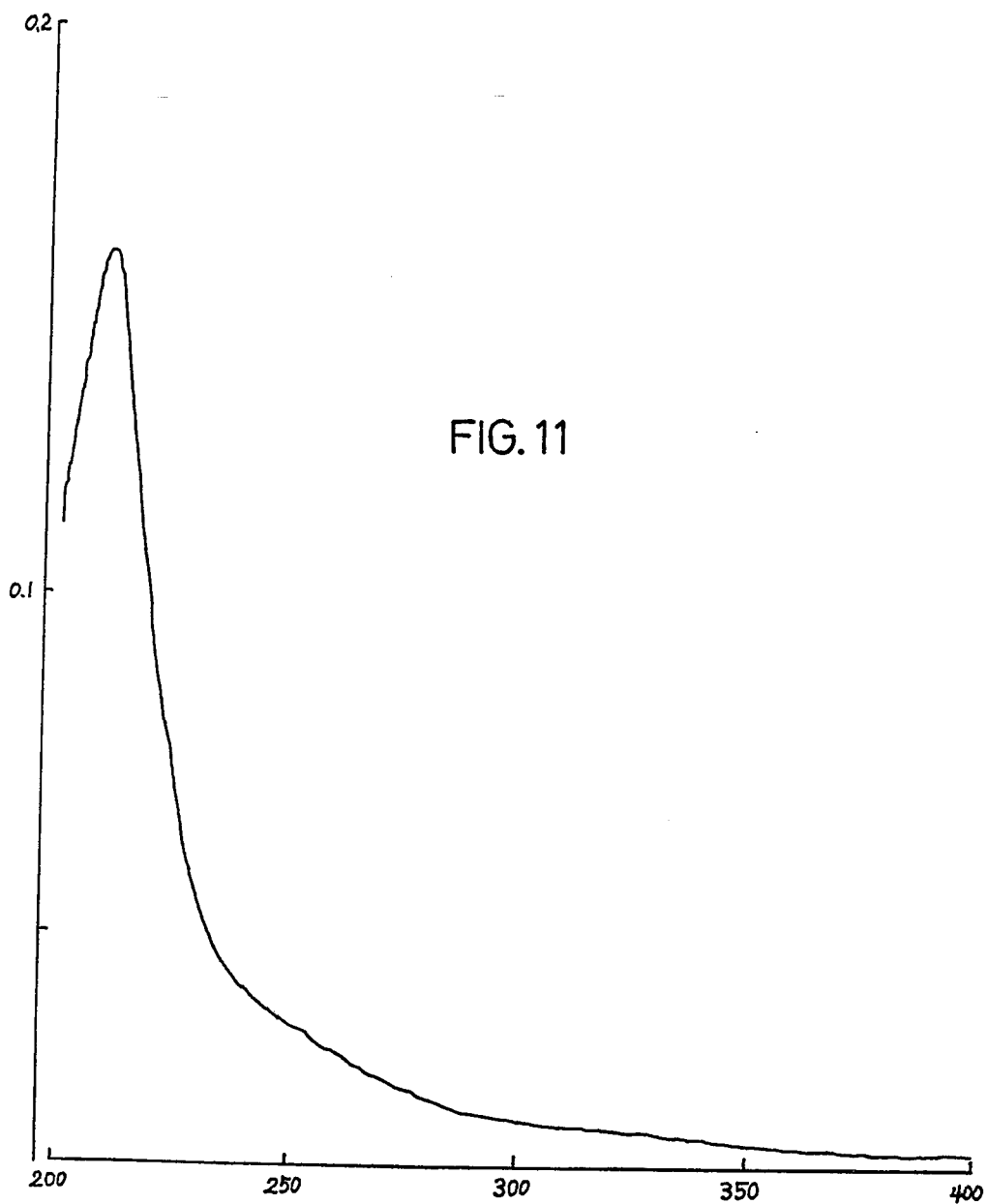

FIGS. 11 and 12 show respectively electron spectrum and CD spectrum of Pt(OH$_2$)(SO$_4$)(cis-l-aamch).

The following non-limitative examples illustrate the invention.

EXAMPLE 1

(A) Trans-cyclohexane-1,2-dicarboxylic acid (8.105 g; racemic modification) is dissolved in conc. sulfuric acid (25 ml) and chloroform (50 ml) and kept at a temperature of 45° C., to which is added sodium azide (3.6 g) in one hour. After this, the solution is stirred for 90 minutes, added with ice water (25 ml) and is added with ether to remove chloroform. Barium carbonate (90 g) is added to the water layer of the solution to effect the neutralization. Barium sulfate is removed from the solution by filtration and the filtrate is concentrated to dryness to result in needle crystals of rac-trans-2-aminocyclohexanecarboxylic acid (referred to as A) having the following characteristics. When a corresponding rac-cis-compound is used as starting material, there is obtained the corresponding cis-compound i.e. rac-cis-aminocyclohexanecarboxylic acid, referred to as B).

| Elemental analysis (calculated as $C_7H_{13}NO_2$): | | | |
|---|---|---|---|
| | H | C | N |
| Calculated: | 58.7% | 9.15% | 9.8% |
| Found (A): | 58.79% | 9.27% | 9.06% |
| (B): | 58.45% | 9.14% | 9.42% |

Melting point: (A) 273° C. (B) 238° C.

(B) The thus-obtained rac-trans-2-aminocyclohexanecarboxylic acid (1.8 g) is dissolved in ethanol. This solution is saturated with hydrogen chloride and refluxed for 7 hours under conditions for saturation with hydrogen chloride. Ethanol is removed from the solution by distillation, and a small amount of water is added to the reaction solution. Ether is distilled off from the reaction solution which is then evaporated under reduced pressure to obtain ethyl ester of rac-trans-2-aminocyclohexanecarboxylic acid having a melting point of 120°–122° C./2 mmHg. When a corresponding cis-compound is used as starting material, there is obtained the corresponding cis-compound having a melting point of 75° C./2 mmHg.

(C) The thus-obtained ester (trans form; 1.54 g) is mixed with hidrazine hydrate (20 ml) and the mixture is refluxed for one hour. After completion of the reaction, the reaction solution is concentrated under reduced pressure to dryness, resulting in needle crystals of rac-trans-2-aminocyclohexanecarbohydrazide having a melting point of 166°–167° C. When an ester of the corresponding cis-compound is used as starting material, there is obtained rac-cis-2-aminocyclohexanecarbohydrazide.

(D) The thus-obtained trans-compound (1.57 g) is dissolved in a mixture of benzene (100 ml) and tetrahydrofuran (150 ml), added with lithium alminium hydride, and refluxed for 7 days. After completion of the reaction, the reaction solution is added with a saturated solution of potassium carbonate to decompose the excess of lithium alminium hydride. After refluxing for 30 minutes, the solution is filtered and the filtrate is distilled under reduced pressure to remove excessive benzene and tetrahydrofuran, resulting in rac-trans-1-aminomethyl-2-aminocyclohexane.

(E) The cis-compound obtained by (C)(3.5 g) is dissolved in a mixture of benzene (150 ml) and ether (150 ml). The mixed solution is added with lithium alminium hydride (2 g) and ether (50 ml) and refluxed for 7 days. After completion of the reaction, lithium alminium hydride is decomposed. After this, the reaction solution is filtered and the filtrate is distilled to obtain rac-cis-1-aminomethyl-2-aminocyclohexane (melting point: 86° C./5 mmHg).

(F) Rac-trans-aamch thus-obtained (17.6521 g) and (+)-dibenzoyltartaric acid (51.7520 g) in an equimolar amount are suspended in water (100 ml) and stirred to prepare a diastereomer which is washed with water several times and is then dissolved in a solvent of water-/ethanol (1:1 v/v) at an elevated temperature. The reaction solution is allowed to stand for a night to give needles of trans-l-aamch having a specific rotation of $[\alpha]_D^{23} = -95.2°$ which is recrystallized by using a similar mixing solvent to the above-mentioned to a furtherly purified trans-l-aamch-diastereomer having a specific rotation of $[\alpha]_D^{23} = -97.78°$. When the rac-trans-aamch and (−)-di-benzoyltartaric acid are used in a similar manner to that described above, it is possible to obtain trans-d-aamch-diastereomer having a specific rotain of $[\alpha]_D^{23} = +99.06°$.

There is also obtained cis-aamch-diastereomer having a specific rotation of $[\alpha]_D^{23} = +91.2°$ or cis-d-aamch-diastereomer having a specific rotation of $[\alpha]_D^{23} = -88.7°$ respectively by using rac-cis-aamch in combination with either (−)-dibenzoyltartaric acid or (+)-dibenzoyltartaric acid.

(G) Each isomer of the diastereomers thus-obtained is suspended or dissolved in water and added with conc. hydrochloric acid to liberate benzoyltartaric acid which is then removed by filtration. With addition of sodium hydroxide, the filtrate is neutralized to liberate diamine. The filtrate is then extracted with ether, and ether is removed by distillation to obtain each of the following isomers:

Trans-l-aamch (absolute configuration: 1R,2S)
Trans-d-aamch (absolute configuration: 1S,2R)
Cis-l-aamch (absolute configuration: 1R,2R)
Cis-d-aamch (absolute configuration: 1S,2S)

By the use of the isomers thus-obtained, it is possible to obtain the platinum complexes of the present invention in the following manner.

(H) Synthesis of PtCl$_2$(aamch)

Figure 1:
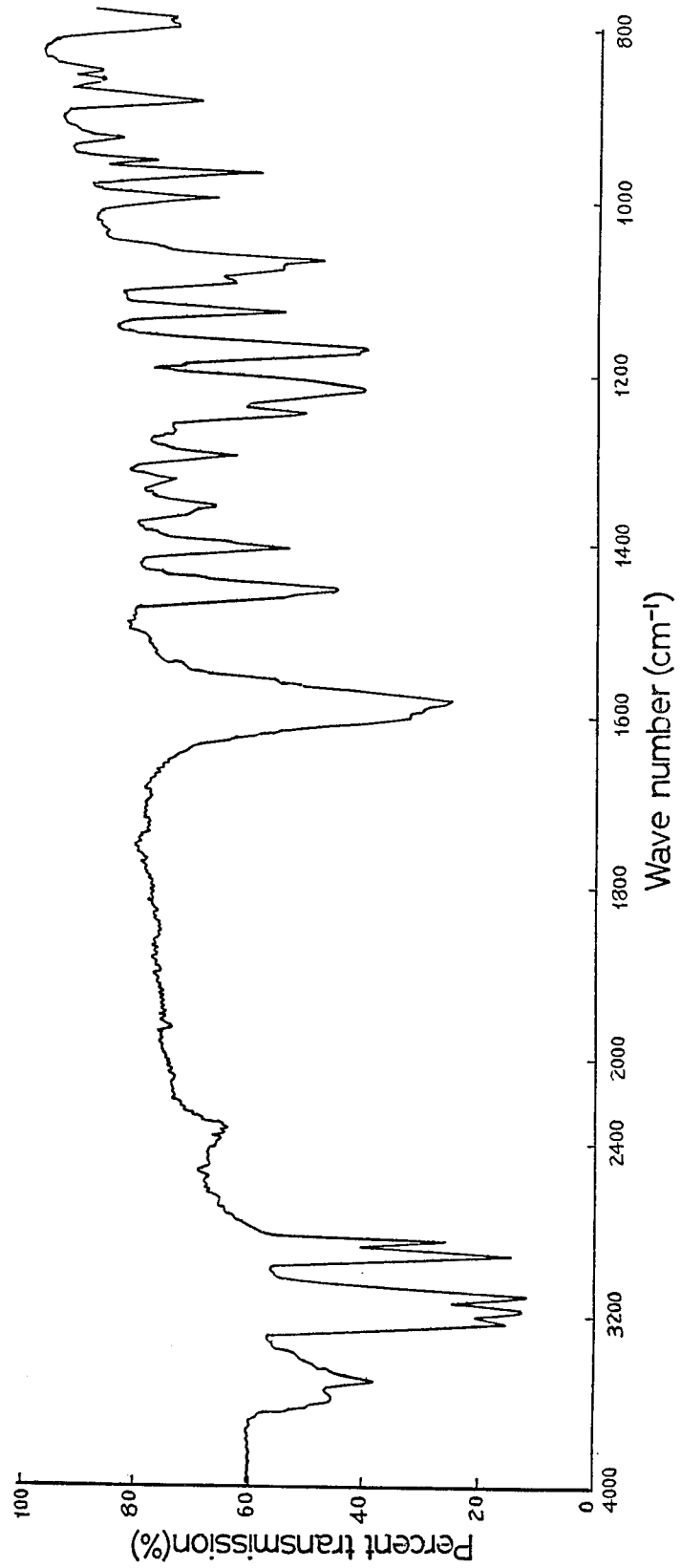
FIGS. 1–6 show respectively infrared absorption spectra of PtCl$_2$(trans-d-aamch), PtCl$_2$(cis-l-aamch), PtBr$_2$(trans-d-aamch), PtBr$_2$(cis-l-aamch), PtI$_2$(trans-d-aamch) and PtI$_2$(cis-l-aamch).
Figure 2:
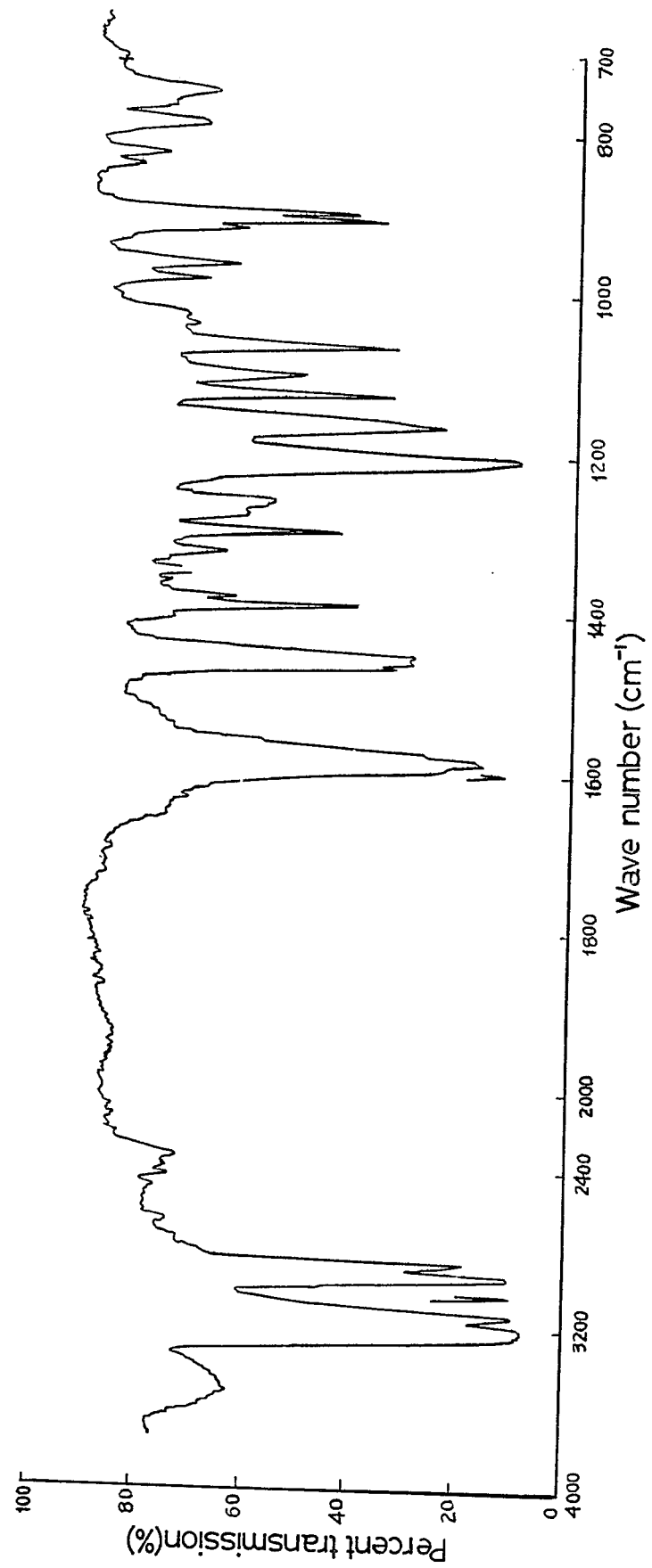
Figure 3:
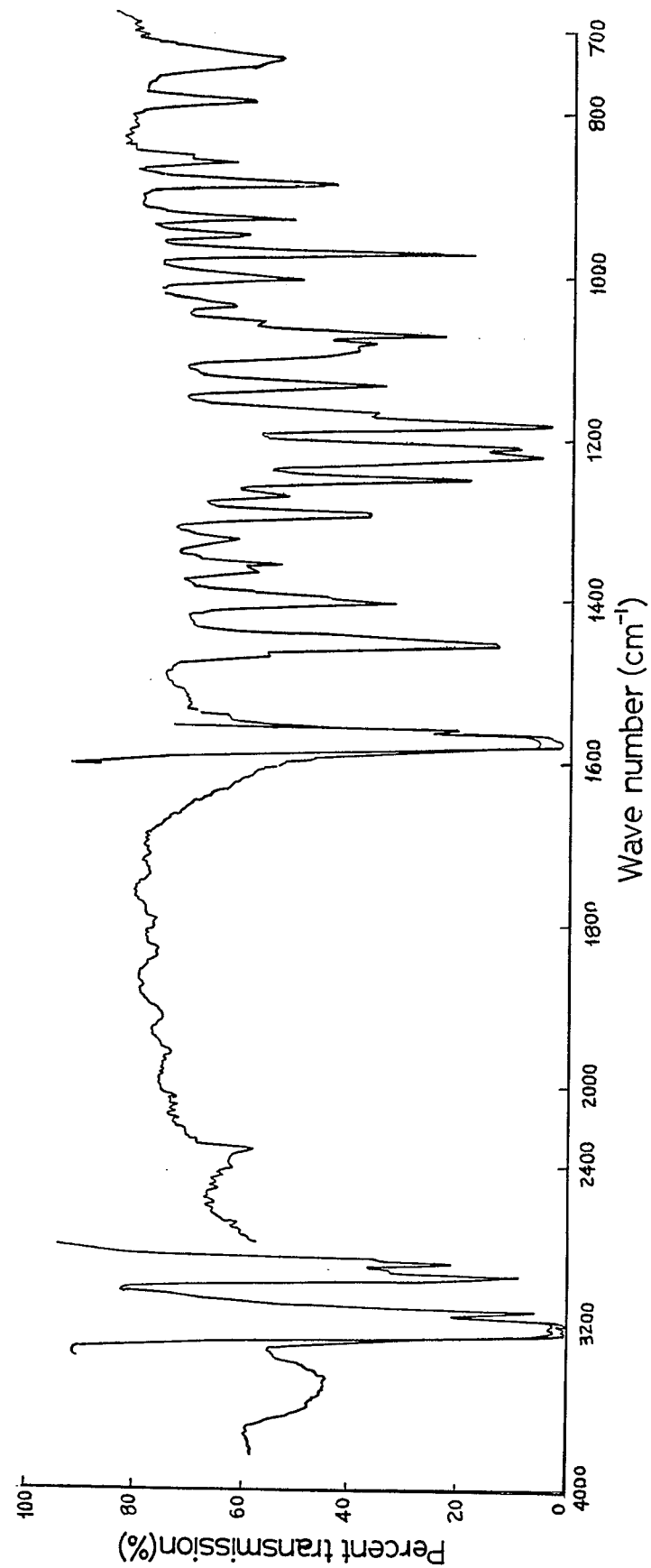
Figure 4:
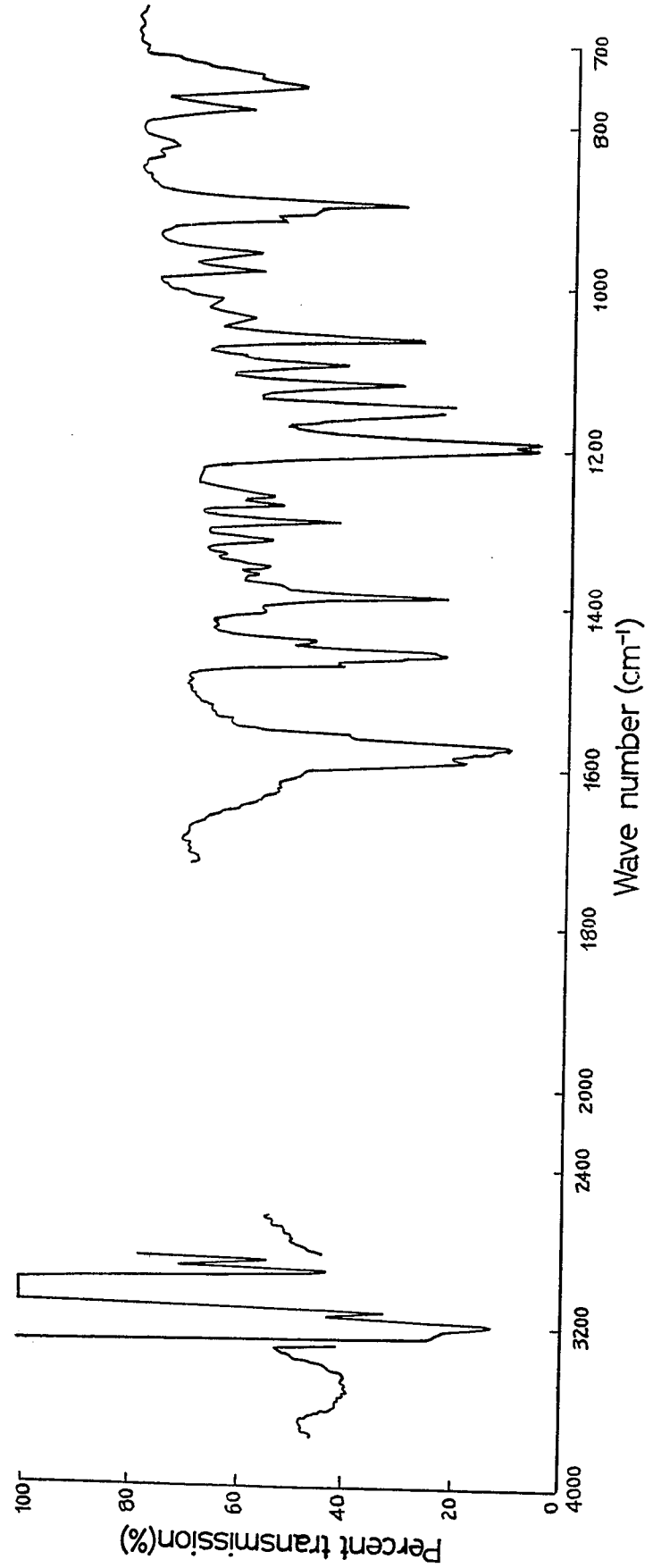
Figure 5:
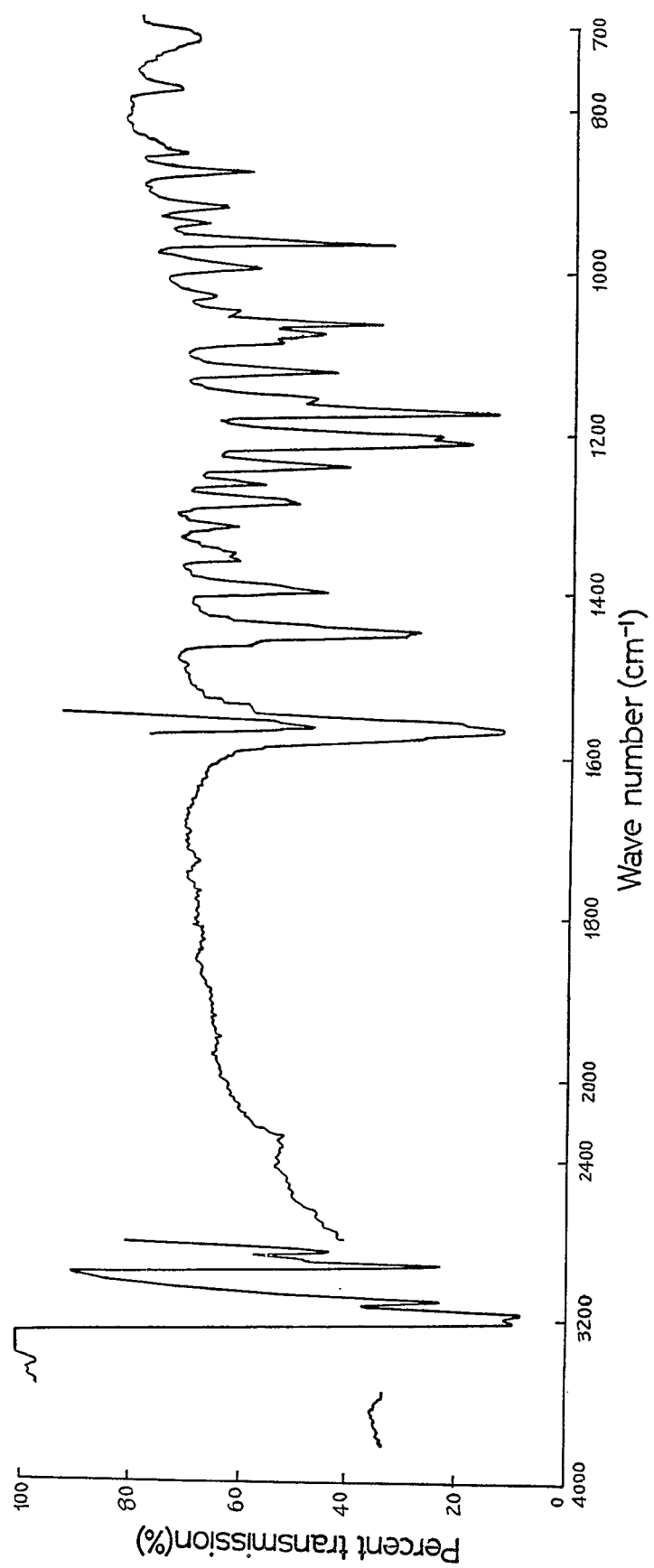
Figure 6:
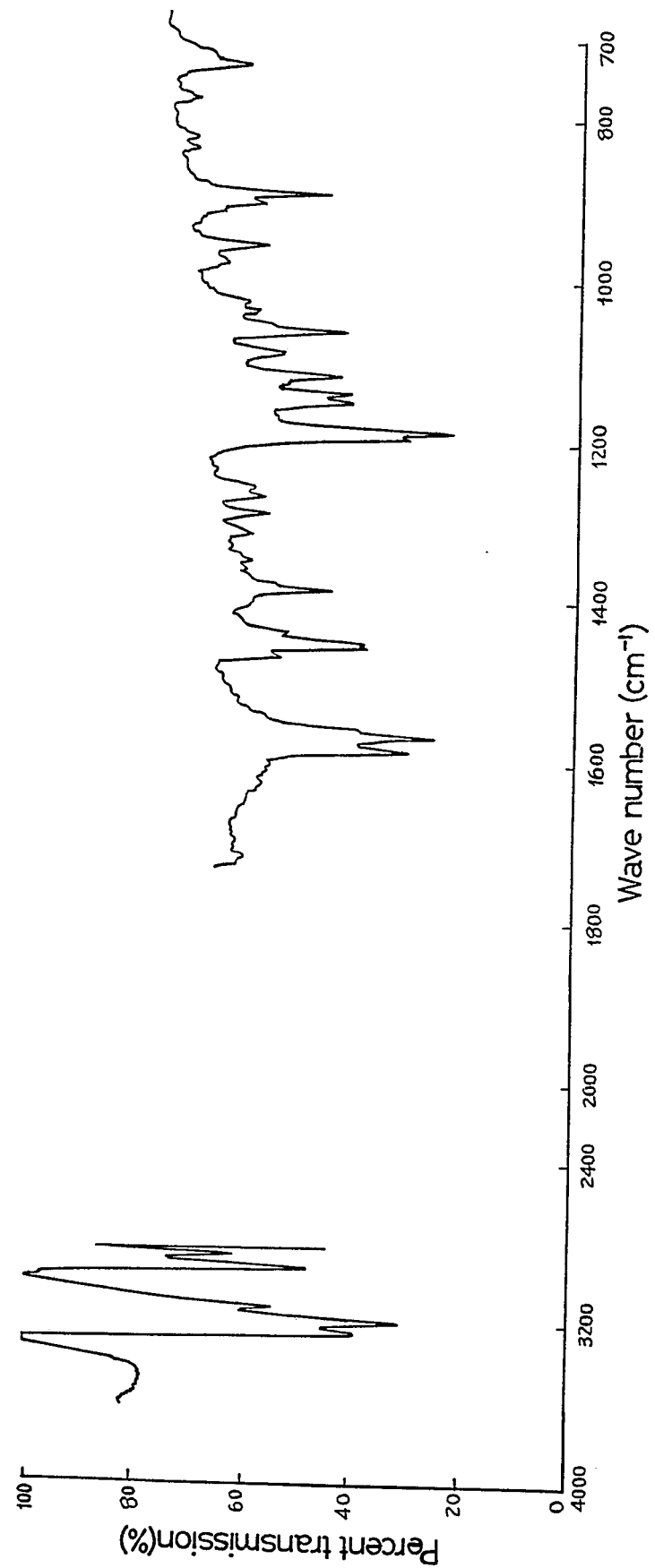

Aamch (1.28259 g) and K$_2$PtCl$_4$ (4.1511 g) are dissolved in water (50 ml) and is allowed to stand for some time to give crystalline precipitates coloured in light yellow to white which represent PtCl$_2$(aamch) corresponding to the aamch used as the starting material. The infrared absorption spectrum of PtCl$_2$(trans-d-aamch) shown in FIG. 1 is identical with that of PtCl$_2$(trans-l-aamch), and the infrared absorption spectrum of PtCl$_2$(cis-l-aamch) shown in FIG. 2 is identical with that of PtCl$_2$(cis-d-aamch).

(I) Synthesis of Pt(NO$_3$)$_2$(aamch), PtBr$_2$(aamch) and PtI$_2$(aamch)

Figure 7:
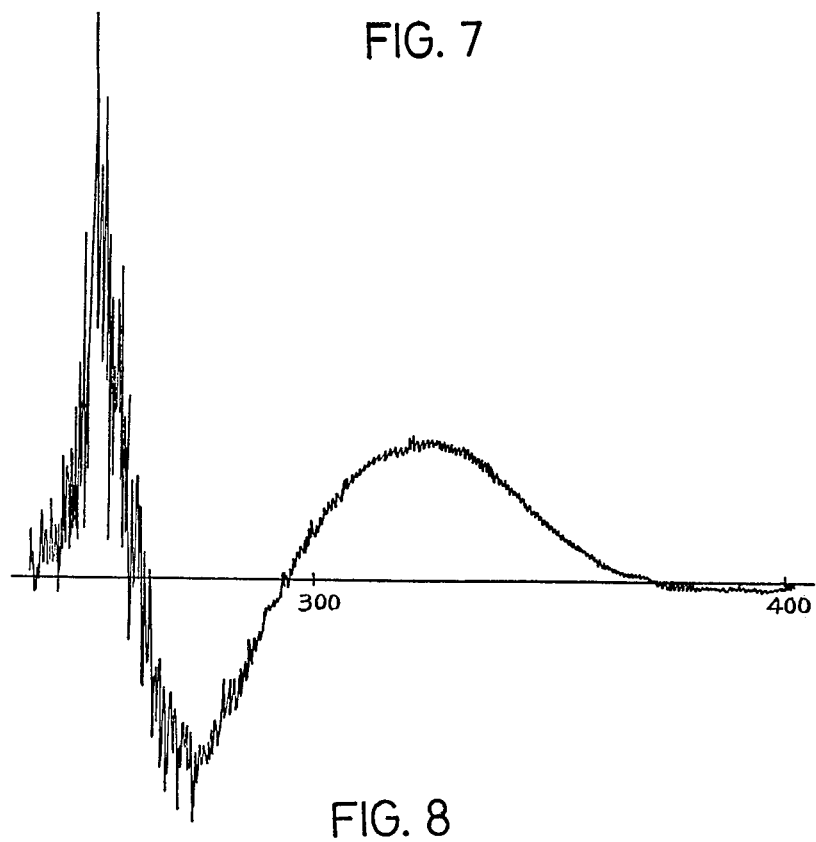
FIG. 7 shows CD spectrum of Pt(NO$_3$)$_2$(trans-l-aamch).
Figure 8:
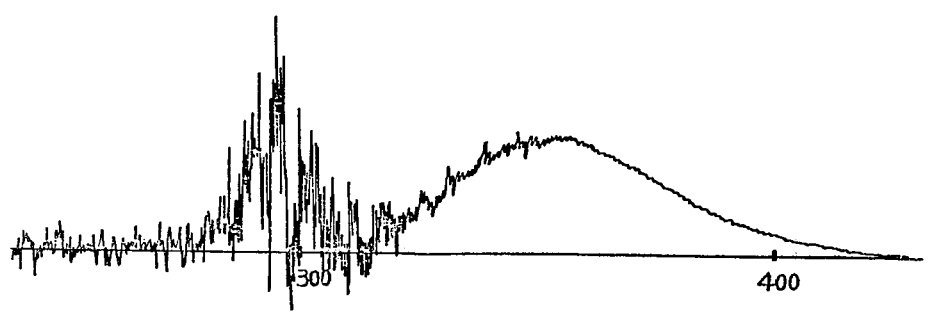
FIG. 8 shows CD spectrum of Pt(NO$_3$)$_2$(cis-l-aamch).

PtCl$_2$(aamch) (3.9424 g) and AgNO$_3$ (3.3974 g) are suspended in water (100 ml) and stirred for a night. The AgCl formed is removed from the solution by filtration and the filtrate is evaporated under reduced pressure to dryness, resulting in Pt(NO$_3$)$_2$(aamch) which is dissolved in water at an elevated temperature and is then added with an excessive amount of KI or KBr to obtain a desired product coloured in light yellow corresponding to the starting PtBr$_2$(aamch) or a yellow product corresponding to the starting PtI$_2$(aamch). The infrared absorption spectra of the thus-obtained PtBr$_2$(trans-d-aamch), PtBr$_2$(cis-l-aamch), PtI$_2$(trans-d-aamch) and PtI$_2$(cis-l-aamch) shown in FIGS. 3–6 respectively are identical with the individual infrared spectra of the corresponding optical antipodes. FIG. 7 shows CD spectrum of Pt(NO$_3$)$_2$(trans-l-aamch) measured at a concentration of $1.788 \times 10^{-2}$ mol ($\Delta\epsilon_{323} = +0.025$, $\Delta\epsilon_{275} = -0.032$). FIG. 8 shows CD spetrum of Pt(NO$_3$)$_2$(cis-l-aamch) measured at a concentration of $3.721 \times 10^{-2}$ mol ($\Delta\epsilon_{355} = +0.020$).

(J) Synthesis of Pt(OX)(aamch), Pt(mal)(aamch) and Pt(gluc)(aamch)

Pt(NO$_3$)$_2$(aamch) (4.4736 g) and potassium oxalate (1.8424 g) are dissolved in water (10 ml) at an elevated temperature and allowed to stand at ambient temperature to obtain platy crystals of Pt(OX)(aamch) coloured in white.

Pt(NO$_3$)$_2$(aamch) (4.4736 g) and sodium malonate (1.6604 g) are dissolved in water (10 ml) at an elevated temperature and the solution is concentrated by heating to make up the amount to 5 ml. By allowing the solution to stand at room temperature for a night, white needles of Pt(mal)(aamch) are obtained.

Pt(NO$_3$)$_2$(aamch) (1.1184 g) and sodium D-glucuronate (0.63049 g) are dissolved in water (5 ml) at an elevated temperature. The solution is allowed to stand at room temperature for a week and is then concentrated under reduced pressure to obtain PT(gluc)(aamch).

(K) Synthesis of PT(OH$_2$)(SO$_4$)(aamch)

PtCl$_2$(aamch) (3.9424 g) and AgSO$_4$ (3.1183 g) are suspended in water (100 ml) and the solution is stirred for a night. After this, the solution is filtered to remove AgCl and the filtrate is concentrated under reduced pressure, followed by addition of acetone to result in white crystals of Pt(OH$_2$)(SO$_4$)(aamch).

Figure 9:
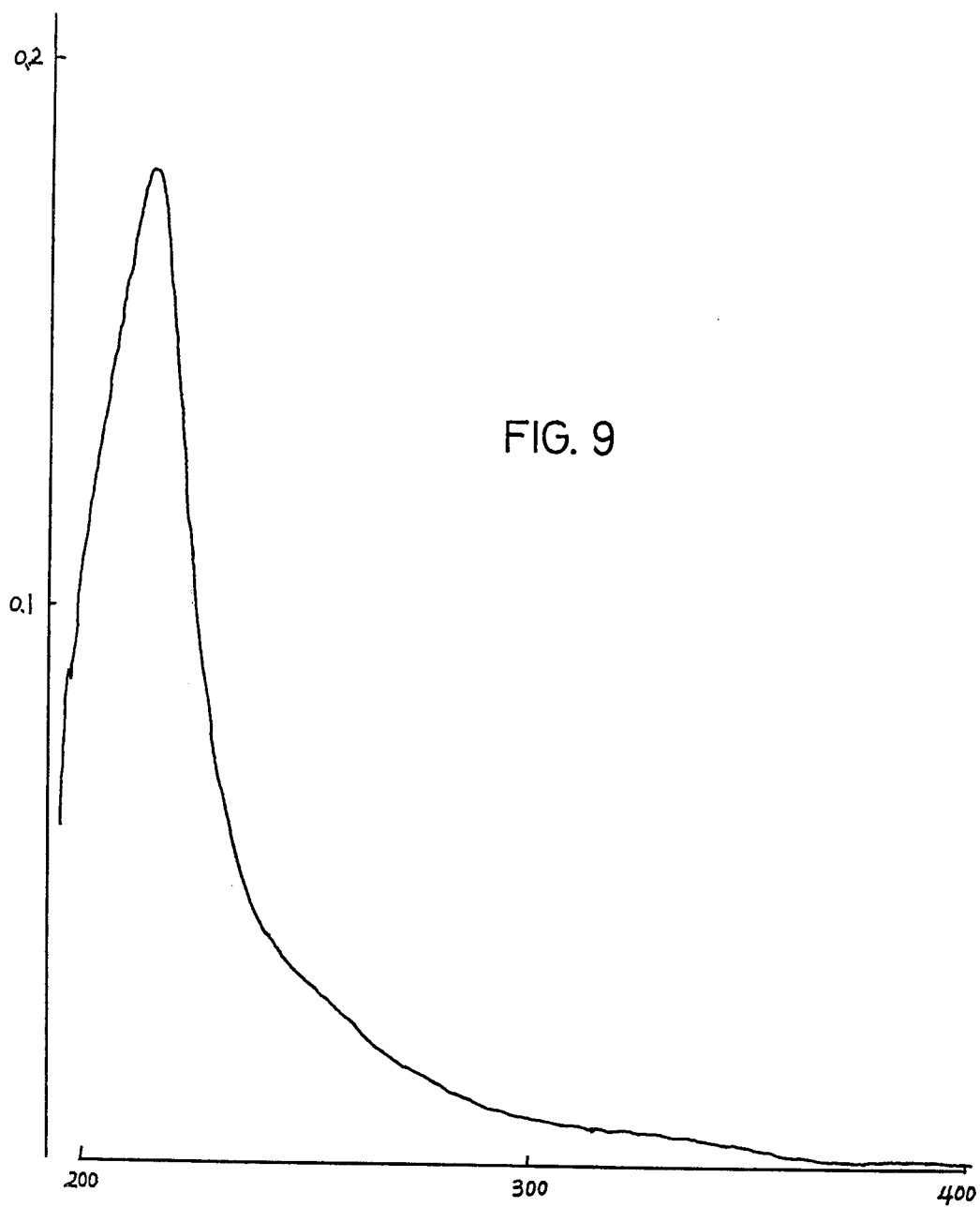
FIG. 9 shows electron spectrum of Pt(OH$_2$)(SO$_4$)(trans-l-aamch).

FIGS. 9 and 10(1) show respectively the electron spetrum of Pt(OH$_2$)(SO$_4$)(trans-l-aamch) [measured at a concentration of $1.163 \times 10^{-3}$ mol by using a quartz cell (length of the optical pass: 1 cm)] and its CD spectrum [measure at a concentration of $1.163 \times 10^{-2}$ mol; $\Delta\epsilon_{321} = +0.039$; $\Delta\epsilon_{272} = -0.030$]. FIG. 10(2) shows the CD spectrum of Pt(OH$_2$)(SO$_4$)(trans-d-aamch) [measured at a concentration of $2.027 \times 10^{-2}$ mol; $\Delta\epsilon_{321} = -0.061$; $\Delta\epsilon_{272} = +0.045$]. FIGS. 11 and 12 show respectively the electron spectrum of Pt(OH$_2$)(SO$_4$)(cis-l-aamch) [measured at a concentration of $7.86 \times 10^{-4}$ mol by using a quartz cell (length of the optical pass: 1 cm)] and its CD spectrum [measured at a concentration of $7.86 \times 10^{-3}$ mol; $\Delta\epsilon_{340} = +0.021$; $\Delta\epsilon_{265} = +0.068$].

What is claimed is:

1. A platinum complex represented by the general formula:

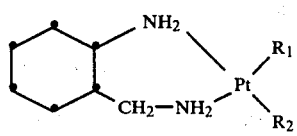

wherein
R₁ and R₂ are same and represent BR, I or NO₃,
or
R₁ is SO₄ and R₂ is H₂O,
or
R₁ and R₂ are bonded with each other to form either
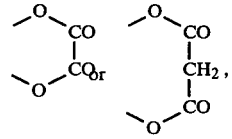
and the configuration of 1-aminomethyl-2-aminocyclohexane is selected from trans-l, trans-d, cis-l and cis-d.
* * * * *